United States Patent [19]

Allington

[11] 4,406,158

[45] Sep. 27, 1983

[54] APPARATUS AND METHOD FOR TEMPERATURE CORRECTION OF LIQUID CHROMATOGRAPHY

[75] Inventor: Robert W. Allington, Lincoln, Nebr.

[73] Assignee: Isco, Inc., Lincoln, Nebr.

[21] Appl. No.: 300,602

[22] Filed: Sep. 9, 1981

[51] Int. Cl.³ ............................................. G01N 31/08
[52] U.S. Cl. .................................... 73/61.1 C; 417/32
[58] Field of Search ...................... 73/61.1 C; 417/32; 222/54, 63

[56] References Cited

U.S. PATENT DOCUMENTS

| | | | |
|---|---|---|---|
| 4,032,041 | 6/1977 | Bruce | 222/63 X |
| 4,043,906 | 8/1977 | Helmer | 73/61.1 C X |
| 4,102,782 | 7/1978 | Saito et al. | 73/61.1 C X |

FOREIGN PATENT DOCUMENTS

211814 4/1968 U.S.S.R. ............................... 222/54

*Primary Examiner*—Anthony V. Ciarlante
*Assistant Examiner*—Joseph W. Roskos
*Attorney, Agent, or Firm*—Vincent L. Carney

[57] ABSTRACT

To reduce errors in a single-stroke, syringe-type high pressure pump caused by changes in temperature, the temperature of the pump is maintained slightly above ambient by a thermostat-heater system. The volume of liquid within the pump is measured by measuring the speed of the motor from a predetermined starting point and changes in ambient temperature are measured and multiplied by the volume to arrive at a volume error figure. Correction factors are multiplied to take into consideration the different coefficients of thermal expansion of the fluid and the cylinder of the pump. The resulting signal controls the motor speed to maintain a constant flow in spite of temperature changes.

37 Claims, 12 Drawing Figures

APPARATUS AND METHOD FOR TEMPERATURE CORRECTION OF LIQUID CHROMATOGRAPHY

BACKGROUND OF THE INVENTION

This invention relates to control systems for liquid chromatographs.

Liquid chromatographs may be considered as including a pump system, a pump control system, a chromatographic column, a collecting system and a monitoring system. The pump system includes one or more pumps for supplying solvents to the chromatographic column under the control of the pump control system. The pump control system controls the rate of flow, the pressure and the composition of mixtures of solvents in the solvent stream applied to the chromatograph column. The chromatographic column includes an injector for injecting a sample or samples into the column, column packing and connections for receiving solvents.

Reciprocating piston pumps are popularly used as mobile phase supplies in conventional high performance liquid chromatography. In such systems, flow rates are on the order of 1 to 5 milliliters per minute; pump displacements are on the order of 50 or 100 microliters per stroke; the chromatographic column inside diameters are on the order of 4 millimeters and the volume of effluent detector at the outlet of the chromatographic column is on the order of 8 to 20 microliters. Sample sizes are on the order of 50 microliters.

Micro-scale analytical high performance liquid chromatographs are known. These chromatographs can attain considerably higher sensitivity by using smaller samples on the order of 1 microliter. Internal column diameters are on the order of ½ to 1 millimeter and the effluent detector volume may be on the order of 0.3 microliter in such systems.

The conventional liquid chromatography reciprocating pumps have several disadvantages when used in these microsystems, such as: (1) at the required flow rates, which are well under 1 milliliter per minute, there are deleterious effects of pump check valve leakage, pump seal leakage and compression of the working fluid during the reciprocating cycle, resulting in poor flow rate accuracy which makes measurement of retention volumes difficult; and (2) fluctuations in the output pressure and flow rate from these pumps aggravate the already serious problem of noise level in the effluent detector.

Single-stroke, syringe-type pumps do not suffer as much from the flow rate inaccuracy and noise problems of reciprocating pumps, but have the disadavtange of being subject to flow rate errors as a result of temperature changes. These errors occur because the cylinder of the pump contains a large volume of solvent compared to the volume of solvent in the column itself. Normally, the temperature coefficient of expansion of the solvent differs from that of the pump walls and thus, as temperatures change, the volume of the fluid in the chamber changes more than the chamber changes to accommodate the increased volume. Consequently, more or less solvent flows from the pump than the programmed amount.

SUMMARY OF THE INVENTION

Accordingly, it is an object of the invention to provide a novel method and apparatus for supplying liquid at low flow rates and at relatively high pressures.

It is another object of the invention to provide a novel method and apparatus for accurately controlling flow rate and/or pressure for micro-scale liquid chromatography.

It is a still further object of the invention to provide a mobile phase supply for micro liquid chromatography with good flow rate control.

It is a still further object of the invention to provide a syringe-type pump for high pressure liquid chromatography that does not have errors in flow rate caused by changes in ambient temperature.

In accordance with the above and further objects of the invention, a syringe-type pump has the temperature of its fluid chamber controlled at a temperature slightly higher than ambient temperature. Changes in the flow rate which would be expected to occur because of the different temperature coefficients of expansion of the fluid and the walls of the pump are calculated and the pump speed altered to maintain the flow rate constant.

Advantageously, the temperature is controlled by measuring the temperature in the pump and using the measured temperature to control heaters within the pump to maintain the temperature slightly above ambient temperature. The error in flow rate caused by differing thermal coefficients of expansion of the fluids being pumped and the pump walls is determined by measuring changes in ambient temperature and the volume of fluid in the pump, obtaining the product of the two and multiplying the signal by a factor which takes into consideration the different thermal coefficients of expansion to obtain a temperature correction signal which is used to correct motor speed.

The volume of effluent in the pump at any one time is determined from a starting signal indicating the position of the piston and a measurement and integration of the speed of the motor of the pump to provide a signal indicating the piston position and thus the volume of fluid in the pump.

From the above description, it can be understood that the control system of this invention has several advantages, such as: (1) it prevents errors in flow rate due to changes in ambient temperature; (2) it compensates for changes in flow rate due to temperature changes; and (3) it permits more reliable and effective operation of the micro-scale chromatographs.

SUMMARY OF THE DRAWINGS

The above-noted and other features of the invention will be better understood from the following detailed description when considered with reference to the accompanying drawings in which.

DESCRIPTION OF THE PREFERRED EMBODIMENT

Figure 1:
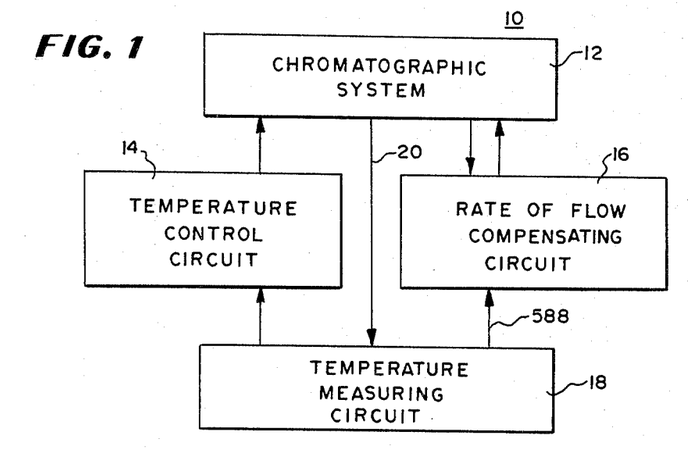
FIG. 1 is a block diagram of an embodiment of the invention.

In FIG. 1, there is shown a block diagram of temperature compensated liquid chromatograph 10 having a chromatographic system 12, a temperature control circuit 14, a rate of flow compensation circuit 16 and a temperature measuring circuit 18.

The temperature measuring circuit 18 is adapted to measure the temperature in the chromatographic system 12 and in the preferred embodiment is electrically connected to the chromatographic system 12 by conductor 20, although it is possible to some embodiments to measure the temperature of the chromatographic system 12 at another location by remote sensors or by sensing the temperature in an enclosure for the chromatographic system 12.

The temperature measuring circuit 18 is electrically connected to the temperature control circuit 14 and to the rate of flow compensation circuit 16. The rate of flow compensation circuit 16 is electrically connected to the chromatographic system 12 to compensate for temperature changes and, in the preferred embodiment, the temperature control circuit 14 is also electrically connected to the chromatographic system 12 although it may be connected to an external heater instead.

In one embodiment, the temperature control circuit 14 receives a temperature measurement from the temperature measuring circuit 18 and stabilizes the temperature in the chromatographic system 12 in response to this temperature. Its purpose is to prevent deviations from the programmed flow rate during a chromatographic run caused by changes in temperature. These deviations would otherwise occur because the different temperature coefficients of expansion of the liquid in a pump and the pump chamber increase the volume of the liquid in the pump chamber more than the size of the chamber increases and thus change some of the flow parameters in the chromatograhic system 12.

In another embodiment, the temperature measuring circuit 18 applies a signal to the rate of flow compensation circuit 16 which controls the rate of flow of fluid to compensate for changes in its size with respect to the size of the conduits or chambers through which it flows. For example, it may change the rate of pumping by controlling the signals to a pump motor to reduce or increase the pumping rate in a manner that compensates for the volumetric changes of the solvents with respect to the pump chambers.

Since the amount of compensation depends on the volume of liquid as well as on the temperature coefficients of expansion and changes in the temperature, the chromatographic system 12 also applies signals to the rate of flow compensation circuit 16 that enables the volume of liquid to be monitored. The difference in temperature coefficients of expansion are entered by the operator and are known in the art. The volume is monitored by measuring the pump speed from a known starting volume determined by pump piston position.

The chromatographic system 12 may be any type of chromatographic system but, in the preferred embodiment, it is the system disclosed in the copending application by Robert W. Allington entitled, "Apparatus and Method of Liquid Chromatography", application Ser. No. 300,567 assigned to the same assignee as this application and filed concurrently herewith. This temperature compensation system 10 is particularly adapted to micro-scale, high pressure liquid chromatographic systems.

In the preferred embodiment, the micro-scale, high pressure liquid chromatographic system 12 may be any suitable type. Generally, micro-scale liquid chromatographs differ from other high-performance liquid chromatographs by using smaller components and flow rates. For example, most commercial high-performance liquid chromatographs use columns of 2 to 4 millimeters in diameter and 25 to 100 centimeters in length. They are operated with carrier flow rates between one-half and three milliliters per minute.

On the other hand, micro-scale liquid chromatographs utilize internal column diameters in the order of one or one-half millimeter and the effluent detector volume may be in the order of three-tenths of a microliter. The samples are on the order of one microliter.

Micro-scale liquid chromatographs are sold under the trademark, FAMILIC-100 M by Jasco International Co., Ltd., 24-21 Sennien-Cho, Hachioji-City, Tokyo 193, Japan. Such units are described in "Micro Instrumentation For Liquid Chromatographs", by F. S. Karasec, Research/Development, January 1977, Volume 28, No. 1, pages 42–44 and 46.

While a micro-scale chromatograph is described in the preferred embodiment and the invention has certain advantages with it, the invention may be used with other types of chromatographs as well. Moreover, it is principally intended for use with syringe-type positive displacement pumps in micro-scale chromatographs to reduce the errors from temperature changes while maintaining the beneficial aspects of those pumps such as low base-line noise and the like. However, it can be used with other types of pumps as well.

In the preferred embodiment, the pump is a syringe pump or pumps controlled by a signal to apply a programmed flow to a column to elute the components thereof. The invention may be used with isocratic systems, gradient systems or other systems including one pump or more than one pump and with systems including one column or more than one column. It can be adapted to operate with any type of column, monitoring or sample injection apparatus but is specifically intended for micro-scale, high pressure liquid chromatographs and has special advantages when used with syringe pumps in such micro-scale, high pressure liquid chromatographs.

Figures 2, 3:
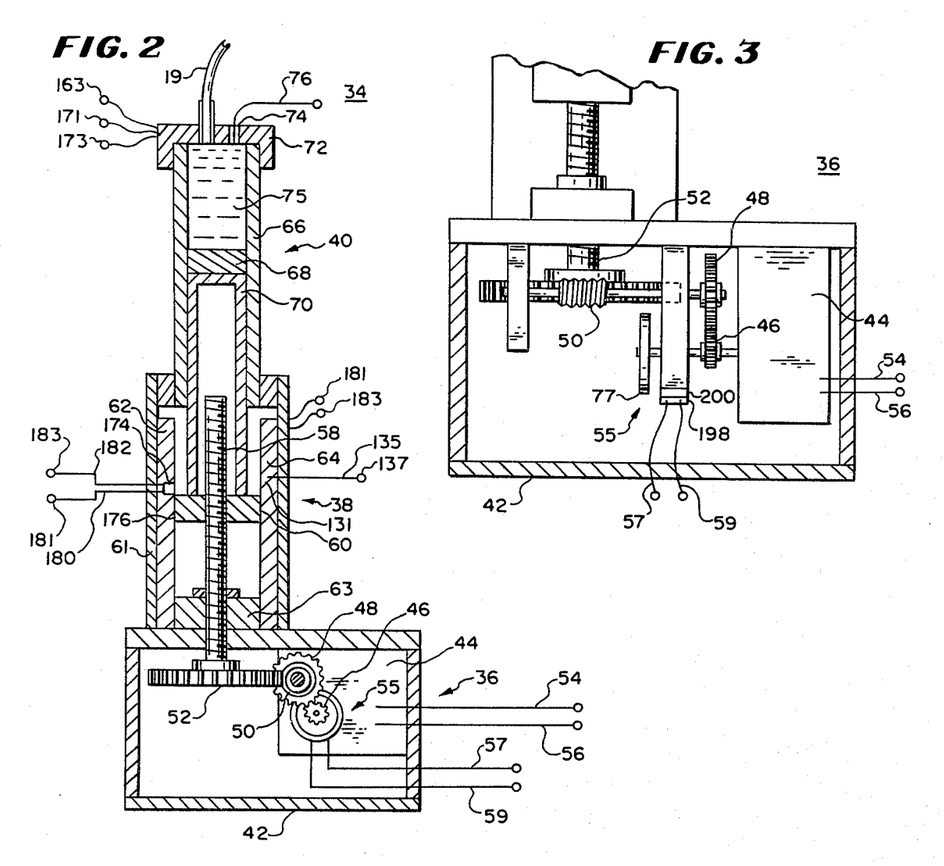
FIG. 2 is a simplified sectional drawing of a pump which may be used in the embodiment of FIG. 1.
FIG. 3 is a sectional view of a portion of the pump of FIG. 2.

In FIG. 2, there is shown a simplified longitudinal section of a typical syringe pump 34 which may be used in the chromatographic system 12 and includes for that purpose, a motor-drive section 36, a piston-drive section 38 and a cylinder section 40 connected together with the motor-drive section 36 driving a screw mechanism in the piston-drive section 38 to force liquid out of the cylinder section 40.

The motor-drive section 36 includes a steel housing 42 in which are mounted a motor 44, an output pinion 46, a gear 48, a worm 50 and a worm wheel 52. The output shaft of the motor 44 turns the output pinion 46 which is engaged with the larger gear 48 and drives it. The worm 50 is mounted along the center axis of the gear 48 and turns with it to drive the worm wheel 52 with an appropriate reduction in speed from the motor 44.

The motor 44 is an electric motor which is driven at a controlled speed which is programmed by a separate pump control system and may be controlled by a feedback servo system or may be another type of accurately controlled motor such as a stepping motor or the like which may be accurately programmed in speed. The speed is controlled by electrical signals applied to conductors 54 and 56 which electrically connect the motor 44 to a source of power outside of the motor-drive section 36.

In one embodiment, a tachometer 55 is mounted in drive section 36. This tachometer 55 generates a signal which is applied to conductors 57 and 59. This signal represents the speed of rotation of the motor 44 and thus the flow rate of fluid through the conduit 19. The tachometer 55 includes a photo-interrupter disc 77 and two sensors 198 and 200 (not shown in FIG. 2) mounted so that the disc 77 turns with the output shaft of the motor 44 to cause the sensors to apply signals to conductors 57 and 59.

To connect the piston-drive section 38 to the motor-drive section 36, the precision bearing 63 supports one end of the lead screw 58 which is mounted to the worm wheel 52 for rotation therewith. The ball nut 60 engages the lead screw 58 which is vertical and perpendicular to the base and thus raises and lowers the ball nut 60 as the motor 44 rotates the worm wheel 52. The ball nut 60 is prevented from rotation by the ball nut guides 62 and 64 which are supported by frame members 61. The lead screw 58 is a ball screw which together with the precision bearing 63 provides a smooth movement upwardly and downwardly of ball nut 60.

The cylinder section 40 includes a cylindrical outer housing 66, a piston head 68, a thrust tube 70 and a cylinder head cap 72. The thrust tube 70 is mounted to the ball nut 60 to be lifted therewith as the ball nut 60 moves upwardly and carries the piston head 68 with it within the cylindrical outer housing 66 into which it fits sealingly against the walls thereof. Solvent is confined in the cylinder compartment 75 so as to be forced upwardly against the cylinder head cap 72 for expulsion through an opening therein.

Within the cylinder head cap 72 is a first opening through which fluid is forced through the conduit 19 to the chromatographic system 12 (FIG. 1) and a second opening which houses a transducer 74 electrically connected to a conductor 76 for applying signals to a pressure measuring circuit described in the aforementioned copending application.

Conductors connected to terminals 181 and 183 provide signals indicating a specific reference piston position to provide a reference volume for purposes to be described hereinafter. Conductors connected to terminals 171 and 173 provide temperature signals and terminals 161 and 163 supply heating current as described hereinafter.

In the microscale chromatographic system using a syringe pump such as 34, certain errors are introduced by changes in temperature which have an effect on the operation of the system because of the large volume of liquid in the cylinder 75 as compared to the size of the chromatographic column (not shown). For example, the effect of a temperature change causes a liquid outflow from the outlet tubing 19 (FIG. 2) upon a rise in the temperature of the pump and its contents. This is because the temperature coefficient of volumetric expansion for the stainless steel and other metal parts enclosing the fluid-holding volume of the pump such as the pump chamber 75 (FIG. 2) have a lower temperature coefficient of volumetric expansion than does the liquid contained in the pump.

As long as heat-dissipating electrical parts are located wall away from the liquid-containing volume of the syringe pump, and preferably, also away from the other metal frame parts of the pump, these temperature changes are dependent mostly upon changes in the ambient temperature in the room around the pump. The error caused by them can be prevented or corrected by temperature control of the pump's cylinder or by measuring temperature change of the pump's cylinder and compensating for resulting expansion or contraction by varying the position of the pump piston.

In FIG. 3, there is an enlarged sectional view of the drive-section 36 illustrating the mounting of the photo-interrupter disc 77 with respect to the sensors 200 and 198. As the motor 44 turns the pinion 46 and its output shaft, it rotates the photo-interrupter disc 77 and the sensors 200 and 198 are interrupted. These photo-interrupter sensors 200 and 198 generate signals on leads 57 and 59 which indicate the direction and the amount of rotation of the motor 44 and thus indicate the flow rate.

To indicate direction, the light paths of the two optical sensors are located apart from each other by a distance equal to an odd multiple of one-fourth of a complete interruption cycle on the photo-interrupter disc 77. Therefore, their outputs are phased ninety electrical degrees apart and the signal on the leads 57 and 59 corresponds to two-phase synchronizing signals well known in the electrical engineering art. Two-phase signals are required to tell the difference between clockwise and counter-clock-wise rotation of the photo-interrupter disc 77.

Figure 4:
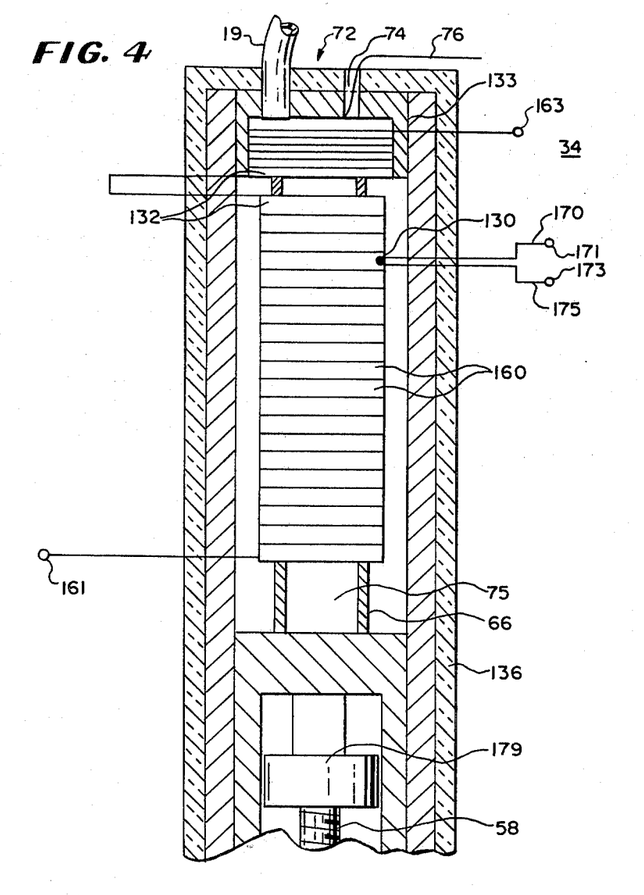
FIG. 4 is a sectional view of another portion of the pump of FIG. 2.

In FIG. 4, there is shown an enlarged section view of the cap 72 of the pump 34 having the outlet conduit 19, the pressure transducer conductor 76, a cap fixture 133, a tubular metal heat conductor 132, a pump cylinder wall 66, a piston (not shown) held in place by a nut (not shown) attached to an overlying tube. The heat conductor 132 formed of two pieces which are forcefitting onto outside of the cap fixture 133 and the outside of cylindrical wall 66.

To measure the temperature within the pump 34, a thermistor 130 is embedded in the lower piece of the two ring-shaped pieces of the heat conducting tube 132 and electrically connected through conductors 170 and 175 to terminals 171 and 173 respectively. To control the temperature within the pump 34, a heat resistance wire 160 is wrapped around heat conducting tube 132 to heat it under the control of potential applied to terminals 161 and 163. The heating wire 160 is helically wound across both sections of the heat conducting tube 132 for maximum heating of both pump cylinder and cap.

To provide for temperature measurements for certain control purposes, a second thermistor 131 (not shown in FIG. 4) is fastened elsewhere in the pump 34 where it will not be directly affected by the heat from the heating wire 160 and is connected through a conductor 135 (not shown in FIG. 4) to a terminal 137 (not shown in FIG. 4) for purposes in connection with the control of the flow rate to correct for heat. The cylinder is surrounded by thermal insulation 136 to further preserve the heat and the heat temperature is maintained approximately one or two degrees Celsius above ambient temperature by the heating wires 160 to thus stabilize the temperature.

To provide further control signals, a push-button switch 174 (not shown in FIG. 4) such as those sold under the trademark, "MICRO-SWITCH", is mounted to the cylinder to contact a cam 176 mounted to move with ball nut 60 attached to the piston 68 to generate a reference signal as the piston moves fully to the top of the cylinder. The push-button switch 174 provides output pulses on conductors 182 and 180 when the piston is in its uppermost position.

Figure 5:
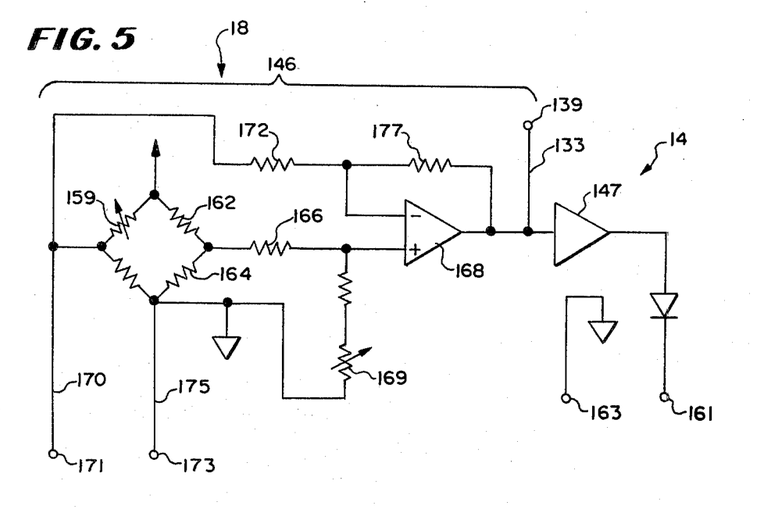
FIG. 5 is a schematic circuit diagram of a portion of the embodiment of FIG. 1.

In FIG. 5, there is shown a schematic circuit diagram of portions of the temperature measuring circuit 18 and the temperature control circuit 14 having a differential amplifier input section 146 in the temperature measuring circuit 18 connected to an output amplifier 147 in the temperature control circuit 14. Terminals 171 and 173 from the thermistor 130 (FIG. 4) supply the measured temperature signal to the differential amplifier circuit 146 and the resulting signal is transmitted to the power amplifier 147 to supply power to terminals 161 and 163 to heat the tubular heat conductive radiator 132 (FIG. 4) and thus maintain the temperature of the cylinder chamber 75 slightly above ambient temperature.

To set the temperature, the differential amplifier input section 146 includes a source of negative potential connected to one diagonal of a bridge, the other diagonal of which is electrically connected to terminal 173 and to ground. The variable resistor 159 has one end electrically connected to the source of negative potential and its other end connected through a second resistor to the opposite diagonal at terminal 173. Resistors 162 and 164 each have one end electrically connected through a resistor 166 to the input of a differential amplifier 168, with the other end of resistor 162 being connected to the source of negative potential and the other end of resistor 164 being grounded.

The non-inverting input terminal of the differential amplifier 168 is grounded through a variable resistor 170 and terminal 171 is electrically connected through conductor 170 and a resistor 172 to the inverting input of the differential amplifier 168. A feedback resistor 177 is connected between the input and the inverting output of the differential amplifier 168. The output of differential amplifier 168 is connected to the input of the power amplifier 147.

The circuit of FIG. 5 has been described in connection with the temperature control circuit 14 (FIG. 1) but may also be used to provide temperature signals to the rate of flow compensation circuit 16 through an output terminal 139 electrically connected to the output of the differential amplifier 168 through a conductor 133. Of course, if the rate of flow compensation circuit 16 is used together with the temperature control circuit 14, a different thermistor will be used such as that shown at 131 (FIG. 2). The reason for this is to space the thermistor away from the heating coils 160 (FIG. 4) when the two are used together.

Figure 6:
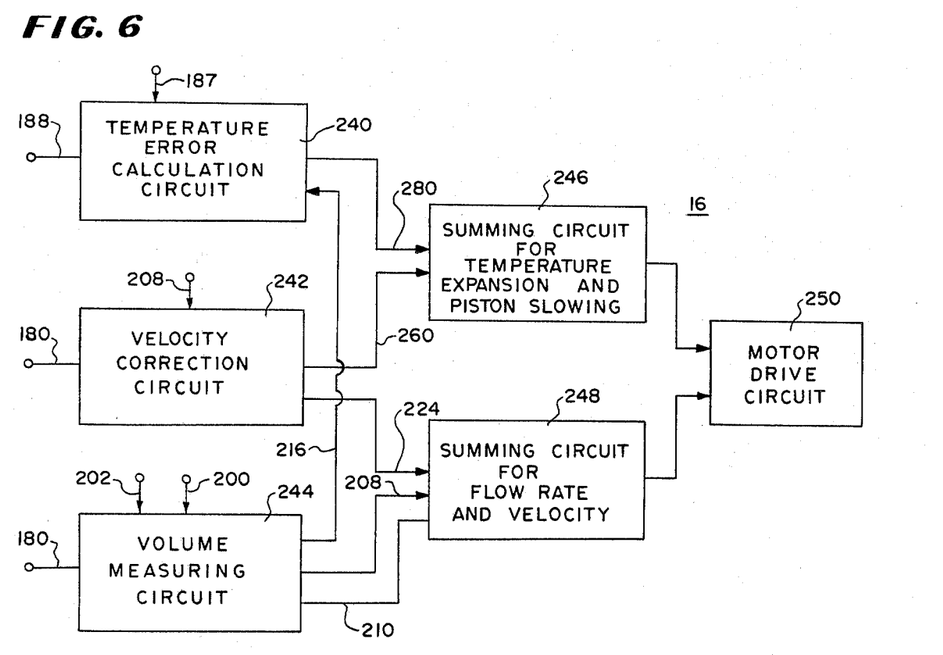
FIG. 6 is a block diagram of a portion of the embodiment of FIG. 1.

In FIG. 6, there is shown a block diagram of the rate of flow compensation circuit 16 having a temperature-error calculation circuit 240, a velocity correction circuit 242, a volume measuring circuit 244, a summing circuit for temperature expansion and piston slowing 246, a summing circuit for flow rate and velocity 248 and a motor drive circuit 250.

The temperature-error calculation circuit 240, the velocity correction circuit 242 and the volume measuring circuit 244 receive signals from the temperature measuring circuit 18 and certain boundary conditions from the chromatographic system 12, and from them, calculate the factors related to the change of velocity of the drive motor necessary to compensate for temperature changes. These signals are summed in the summing circuit for temperature expansion and piston slowing 246 and the summing circuit for flow rate and velocity 248 and applied to the motor drive circuit 250 to control the speed of the pump motor 44 (FIG. 2).

Figure 7:
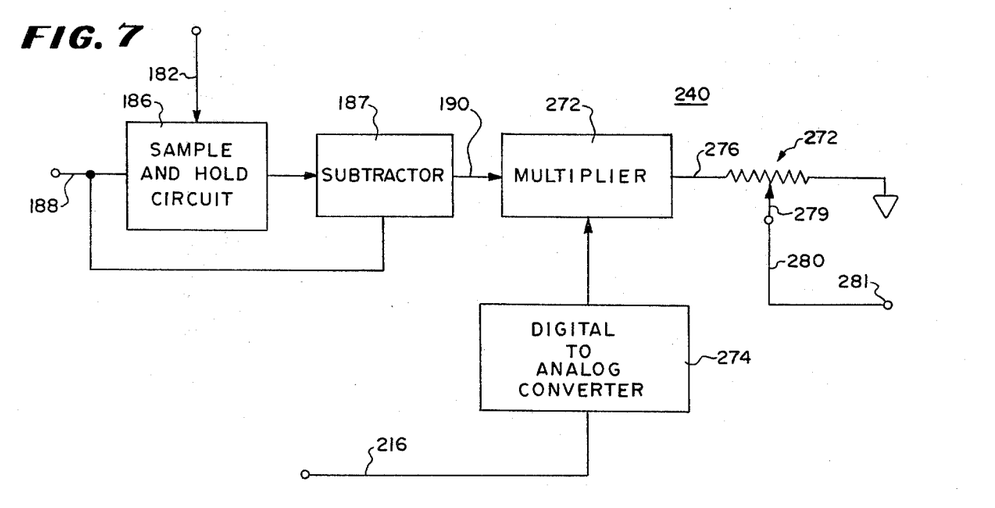
FIG. 7 is a schematic circuit diagram of a portion of the embodiment of FIG. 6.

In FIG. 7, there is shown a schematic circuit diagram of the temperature-error calculation circuit 240 comprising a sample-and-hold circuit 186, a subtractor 187, a multiplier 272, a potentiomenter 278 and a digital-to-analog converter 274. The conductor 188 which receives the temperature signal from the thermistor 131 or the thermistor 130 is electrically connected to the input of the sample-and-hold circuit 186 and to one input of the subtractor 187. Conductor 182 which receives a reset signal from the push-button switch 174 (FIG. 2) is electrically connected to the sample-and-hold circuit 186 to cause it to store the reference potential received on conductor 188 just before the filled cylinder is used to supply liquid to the column.

Subtractor 187 has one input electrically connected to the output of the sample-and-hold circuit 186 and one input electrically connected to conductor 188. Its output conductor 190 is electrically connected to the multiplier 272, so that the sample-and-hold circuit 186 stores a reference potential from conductor 188 at the beginning of a cycle as a result of the signal received on conductor 182 and the output on conductor 190 of the subtractor 187 tracks changes in temperature since it provides to output conductor 190 the difference between new temperatures and the stored reference temperature.

To provide an output signal representing volume changes due to the temperature coefficients of expansion of the fluid, the multiplier 272 has one input electrically connected to output conductor 190 and the other electrically connected to the output of the digital-to-analog converter 274. The input of the digital-to-analog converter 274 receives signals on conductor 216 indicating the position of the piston in the pump (FIG. 4) and converts it to an analog signal which is proportional to the volume of liquid in the chamber. The multiplier 272 multiplies the volume of fluid by the temperature change and provides a signal on conductor 276 proportional to those two factors.

To insert a factor representing the difference in the temperature coefficients of expansion and the geometry of the fluid and pump cylinder, the potentiometer 278 includes a wiper 279 which is adjusted by the operator to the difference between the coefficients of the expansion of the walls of the chamber and the fluid and the geometry to provide a signal on conductor 280 representing the change in the rate of flow of fluid from that programmed into the pump caused by the differences in the temperature coefficients of expansion of the syringe pump and the fluid within the syringe pump. The adjustment is determined experimentally by measurement or may be calculated from geometry, materials and tables in a manner known in the art. The signal on conductor 280 is applied to terminal 281.

Figure 8:
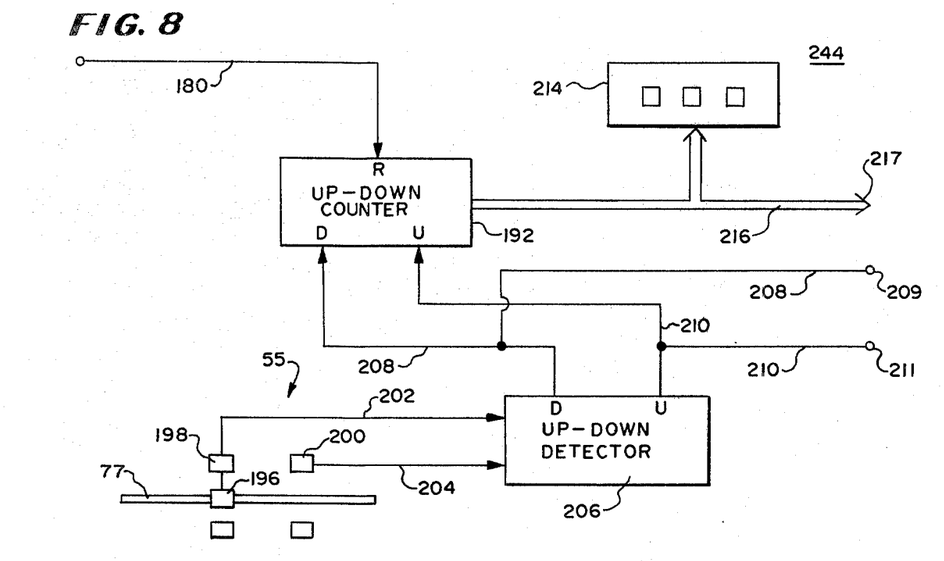
FIG. 8 is a schematic circuit diagram of a portion of the embodiment of FIG. 6.

In FIG. 8, there is shown a schematic circuit diagram of the volume measuring circuit 244 having an up/down counter 192, a motor tachometer 55, an up/down detector 206 and a digital readout circuit 214.

The motor tachometer 55, as described in connection with FIGS. 2 and 3, includes an interruptor 57 and two sensors 198 and 200 which are spaced apart to detect the direction of rotation of the interruptor 57. The interruptor 57 is attached to rotate with the motor so that the sensors 198 and 200 apply signals through conductors 202 and 204 to the up/down detector 206 indicating the direction and the amount of movement of the piston in the pump 34 (FIGS. 2-4).

The up/down detector 206 provides signals on conductors 208 and 210 to the up/down counter 192. The up/down counter 192 is reset by signals on conductor 180 from the Microswitch 174 (FIG. 2) and then begins counting in accordance with signals supplied to its down input terminal and its up input terminal through conductors 208 and 210. The counter counts up for downward (i.e. filling) movement of the piston and down for upward movement (i.e. discharging movement) of the piston. It is electrically connected to digital data conductor 216 which contains binary digit lines indicating the position of the piston in the pump 34 (FIGS. 2-4) and thus the volume of fluid within the cylinder chamber 75. This signal is applied to digital readout circuit 214. Conductors 208 and 210 are electrically connected to output terminals 209 and 211 and digit line conductor 216 is applied to an output terminal 217.

Figure 9:
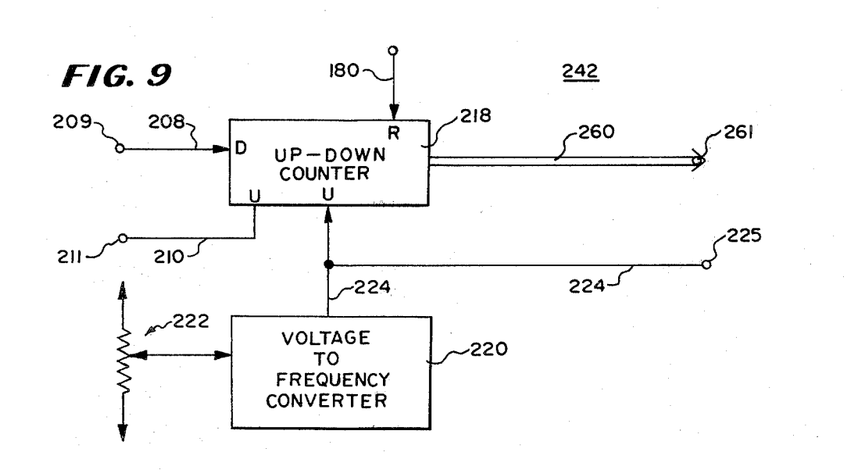
FIG. 9 is a schematic circuit diagram of another portion of the embodiment of FIG. 6.

In FIG. 9, there is shown a schematic circuit diagram of the velocity correction circuit 242 having an up-down counter 128, a voltage-to-frequency converter 220 and a potentiometer 222. The wiper of the potentiometer 222 is electrically connected to the input of the voltage-to-frequency converter 220.

The output of the voltage-to-frequency converter 220 is connected through a conductor 224 to output terminal 225 and to a first up input of the up/down counter 218. The down input of the up/down counter 218 is electrically connected to conductor 208 at output terminal 209 to receive down-counting pulses from the up/down detector 206 (FIG. 8) representing movement of the piston 68 (FIG. 2) upwardly (fluid discharging movement). It counts up from up-counting pulses on line 210 to its second up input as the piston fills the cylinder (moves down and additionally counts up at a rate governed by the voltage-to-frequency counter 220). The output of the up down counter 218 is applied through digital data line conductor 260 to an output terminal 261.

To reset the up/down counter 218, the conductor 180 is connected to its input terminal so it is reset to zero when the piston is in its uppermost position so as to trigger Microswitch 174 (FIG. 2).

The voltage-to-frequency converter 220 counts at a frequency set on potentiometer on 222 to be equal to the programmed flow rate of the pump so that the up/down counter 218 records a number which represents the difference between the programmed flow rate and the actual movement of the piston 68. This difference signal is transmitted to output terminal 261. Output terminal 225, of course, receives pulses at a frequency representing the programmed flow rate.

Figure 10:
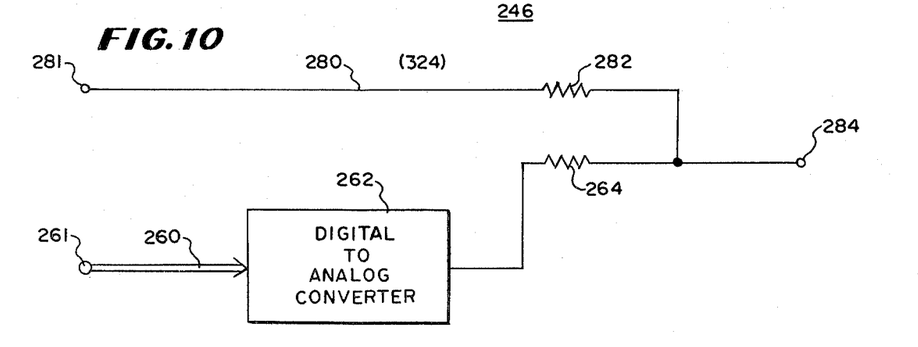
FIG. 10 is a schematic circuit diagram of another portion of the embodiment of FIG. 6.

In FIG. 10, there is shown a schematic circuit diagram of the summing circuit for temperature expansion and piston position error 246 having a digital-to-analog converter 262 and resistors 282 and 264. The digital-to-analog converter 262 has its input electrically connected to conductor 260 and its output connected to terminal 284 through resistor 264 and the resistor 282 is electrically connected at one end to the terminal 284 and at its other end to input terminal 281 through a conductor 280.

The digital-to-analog converter 262 receives signals from the up/down counter 218 (FIG. 9) representing the position error in the movement of the piston, converts these signals to analog form and applies the analog signal to a summing node at terminal 284. Terminal 281 receives analog piston position signals indicating the accumulated error in flow rate caused by the different temperature coefficients of expansion causing a difference between the expansion or the contraction of the fluid at the expansion or the contraction of the chamber 75 and applies the analog signal to the summing node 284 so that the summing node 284 sums the errors in instantaneous position caused by temperature coefficients of expansion and by changes in the flow rate.

Figure 11:
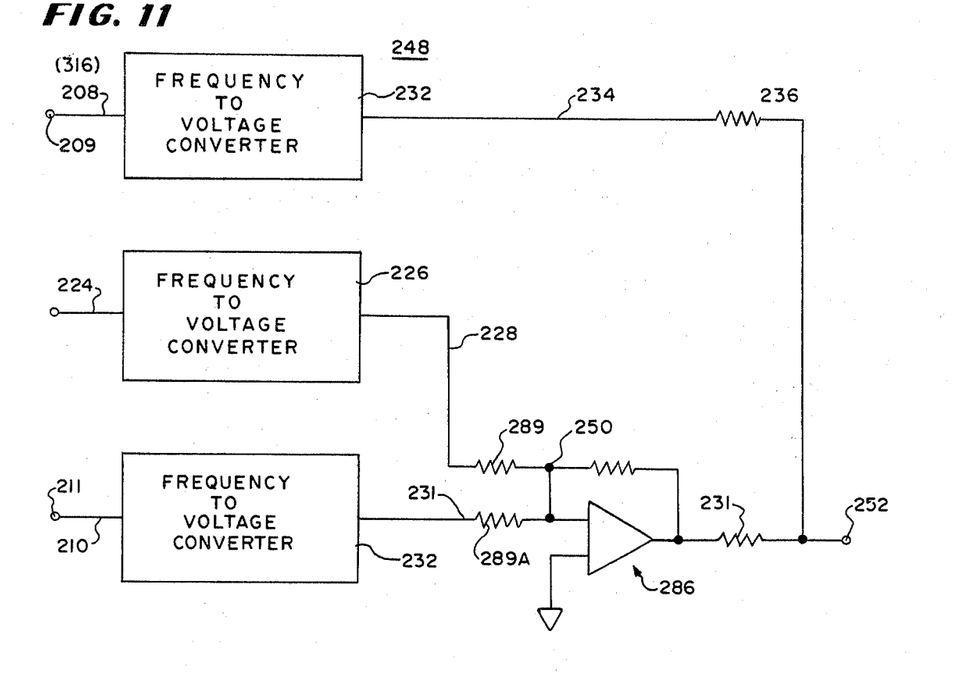
FIG. 11 is a schematic circuit diagram of another portion of the embodiment of FIG. 6.

In FIG. 11, there is shown a schematic circuit diagram of the summing circuit for flow rate and piston velocity 248 having a frequency-to-voltage converter 232, a frequency-to-voltage converter 226, a frequency-to-voltage converter 230, an operational amplifier inverter circuit 286, a resistor 236 and a resistor 288.

The frequency-to-voltage converter 232 receives signals on conductor 210 indicating downward direction travel velocity of the piston 68 and it converts those signals to an analog voltage for application to the summing terminal 250 through resistor 288A to indicate downward piston velocity and thus upward rate of change of volume of the cylinder.

The frequency-to-voltage converter 226 receives pulses on conductor 224 from the velocity correction circuit 242 indicating the set flow rate and converts those pulses to an analog signal which is applied to the summing terminal 250 through resistor 287, through the operational amplifier 286, to the resistor 288 and then on to summing terminal 252.

The frequency-to-voltage converter 230 receives signals on conductor 208 indicating upward travel velocity of the piston 68 and converts those signals to an analog potential which it applies through line 234 to the resistor 236 to the summing terminal 252.

Figure 12:
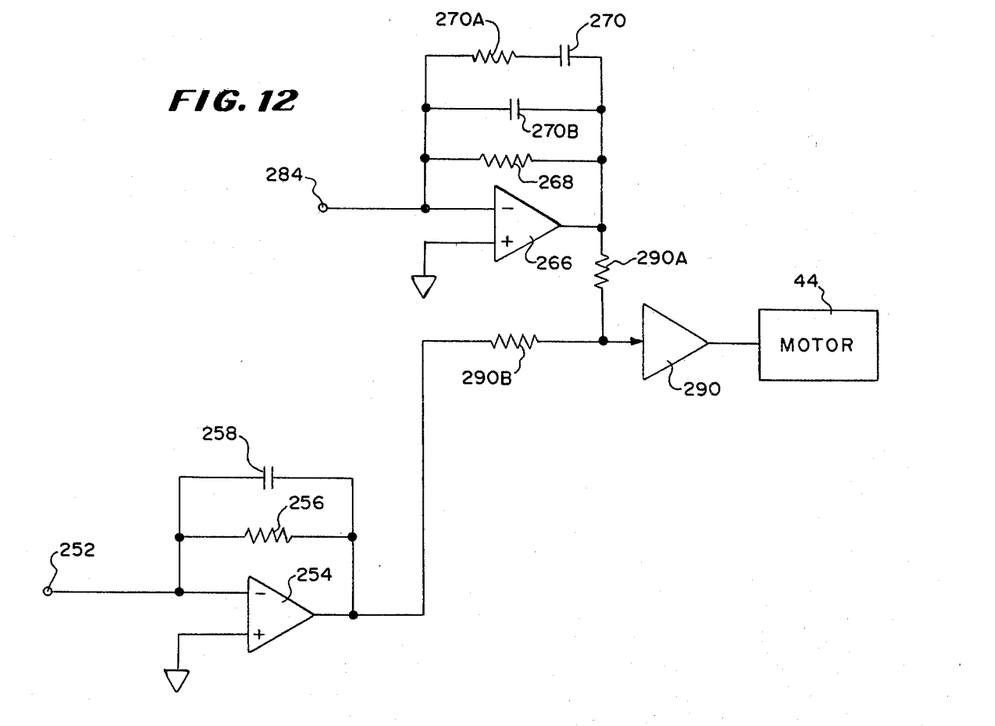
FIG. 12 is a schematic circuit diagram of still another portion of the embodiment of FIG. 6.

In FIG. 12, there is shown a schematic circuit diagram of the motor drive circuit 250 having a first operational amplifier 254, a second operational amplifier 226 and an operational power amplifier 290 adapted to drive the motor 44. Operational amplifier 266 has its inverting input terminal electrically connected to its summing node at terminal 284 to apply temperature change and accumulated piston position error signals through resistor 290A to the summing node of operational amplifier 290. Operational amplifier 254 has its inverting input electrically connected to conductor 252 and its output connected to the summing node of operational amplifier 290 to provide a signal indicating velocity error. These signals are applied by the operational amplifier 290 to the motor 44 to control its speed.

In, operation, the pump cylinder can be controlled to a constant temperature by means of negative temperature coefficient thermometer sensor 130 (FIG. 4) embedded in ring-shaped heat conductor 132 which carries the resistance heaving wire and is force-fitted onto pump cylinder wall 66 (FIG. 2). In such case, it may be advisable for the thermistor used in conjunction with the circuit of FIG. 7 to be the other thermistor 131, located elsewhere on the pump.

The signal from the temperature sensor on leads 170 and 175 to the bridge circuit composed of items 159, 160, 162 and 164 are led differential amplifier circuit 146 composed of items 166 through 174. Control 159 selects the temperature setpoint. The output of the differential amplifier is led to a non-inverting heater power amplifier 147. The output current of the heater power amplifier 147 is fed through an anti-reversing diode to resistance heating wire 160 wrapped on heat conductor 132 on cylinder walls 66 and pump cylinder cap 72.

The setpoint control 159 is set to a temperature a few degrees centigrade above room temperature. This controls the pump cylinder 75 and its contents to a constant temperature, eliminating almost all the pump displacement error resulting from "thermometer effect". Thermal insulation 136 (FIG. 4) surrounds the pump cylinder 75 to lessen the effect of ambient temperature changes upon the pump cylinder 75 and its contents. This increases the accuracy of control. A disadvantage with this method is that it can take several hours for the pump temperature to equilibrate after turning the solvent delivery system on or after refilling the pump chamber with fresh mobile phase liquid.

Another approach is to vary the position of the piston within the pump so that the piston displacement equals the change in volume due to the effect of temperature change acting upon the liquid contents of the pump. The piston position is made to change differentially to correspond to a volume difference proportional to the instantaneously contained volume in the pump times the difference in temperature coefficient between the solid "steel" parts of the pump and the liquid contents of the pump, times the positive or negative temperature difference between the current temperature and the temperature at which the pump is put into operation as described below.

The thermistor 130 (unless this thermistor is used to control the pump temperature, in which case it would be thermistor 131 and a second circuit such as that shown in FIG. 5 measures the temperature of the pump cylinder. It may be connected to a circuit such as 18 to provide a potential on terminal 137 (FIGS. 4, 5 and 7). This potential is connected through conductor 188 to sample-and-hold circuit 186. Microswitch 174 is tripped by cam 176 (FIG. 4) mounted on nut 178 which is connected to the piston 68 through tube 179.

When the piston 68 is all the way up in the cylinder (when the volume inside the cylinder is very close to zero), microswitch 174 is depressed and a signal indicating near-zero pump internal volume is put out on leads 182 and 180. This causes sample-and-hold circuit 186 (FIG. 7) to track the amplified temperature signal from thermistor 130 or 131 (FIG. 4) on line 188. At this time the output voltage on line 190 goes to zero; representing the setting of a reference temperature to equal the actual temperature.

The position of the piston is digitized and put in up/down counter 192 (FIG. 8). The numeric contents of up/down counter 192 (FIG. 8) indicates the location of the piston within the pump cylinder and therefore indicates the volume contained in the pump chamber.

To digitize the piston position, the optical tachometer disc 77 (FIGS. 3 and 8) is fastened to shaft 196 of motor 44. The tachometer disc forms an optical interruptor which works in cooperation with optical-interruptor sensors 198 and 200. Electric signals indicating lighpath interruption are sent on leads 202 and 204 to up/down detector 206.

The lightpaths of the two optical sensors are located apart from each other by a distance equal to an odd multiple of one-fourth of a complete interruption cycle on optical interruptor disc 194. Therefore their outputs on leads 204 and 202 are phased ninety degrees apart and the signal on these two leads corresponds to the two-phase synchronizing signals well known in the electrical engineering art. Two-phase signals are required to tell the difference between clockwise and counterclockwise rotation of optical interruptor disc 77.

Up/down detector 206 converts this two-phase signal into a stream of output pulses placed on line 208 at the output of up/down detector 206 when optical interruptor disc 77 rotates in a direction corresponding to upward movement of the piston within the cylinder; and up/down detector 206 also puts pulses on lines 210 which corresponds to optical interruptions when the disc turns in the direction corresponding to downwards movement of the piston. Leads 210 and 208 are respectively brought to the up-count input and down-count inputs of up/down counter 192.

When the piston is at the top of a cylinder and the volume inside the cylinder is close to zero, microswitch 174 puts a signal on line 180 (FIG. 8) that resets the up/down counter 192 to zero, indicating zero volume. This volumetric content is read out on digital display 214 which operates from the parallel output leads 216 of up/down counter 192. Up-count pulses on line 210 (corresponding to downward movement of the piston) cause up/down counter 192 to count upwards from zero. Counter 218 (FIG. 9) counts downward on down pulses placed on line 208 by up/down detector 206 in response to upward movement of the piston. Counter 218 counts upward on "up" pulses put on line 210 by detector 206 in response to downward movement of the piston.

Up/down counter 218 also is caused to count upward by pulses at a second up input on line 224 from voltage-to-frequency converter 220 which is connected to the operator's flow rate control 222.

Pulses on 224 also are brought to the input of frequency-to-voltage converter 226 (FIG. 11) which produces an output on line 228 which is proportional to the flow rate setpoint. The signal on lead 210 at the input of frequency-to-voltage converter 232 is proportional to the downwards travel speed (if any) of the piston. The converter outputs on lines 228 and 231 are brought respectively through resistors 289 and 289A by summing node 250 through amplifier 286 and on to summing node 252 through resistor 231.

The output of frequency-to-voltage converter 230, whose input is line 208, is led by lead 234 to input resistor 236, to the summing node at terminal 252 of the velocity-error amplifier composed of operational amplifier 254, gain-setting resistor 256 and noise-smoothing capacitor 258 (FIG. 12). The output of amplifier 254 is a voltage proportional to the instantaneous velocity error of the piston.

The output on parallel leads 260 from up/down counter 218 (FIG. 9) is a digital signal indicating the instantaneous deviation of the piston position from the desired location but not including temperature compensation. This position-error is converted by digital-to-analog converter 262 to a voltage which is placed on input resistor 264 (FIG. 10) to the position-error amplifier composed of operational amplifier 266 (FIG. 12), gain-setting resistor 268, stabilizing and noise reducing capacitor 270 and resistor 270A and noise reducing capacitor 270B.

The position-error applied to the left side of resistor 282 (FIG. 10) is the position-error caused by the temperature constant. If there is a temperature change during operation, the voltage on line 190 (FIG. 7) increases by an amount representing the actual temperature change. This is led to an analog multiplier 272 or to the analog input of a two-quadrant multiplying digital-to-analog converter (not shown). If an analog multiplier is used, a digital-to-analog converter 274 supplies the output to its other input. The digital input of the digital-to-analog converter or two-quadrant multiplying digital-to-analog converter is a digital input representing the parallel piston-position signal on line 216.

The produce, which is proportional to the volume of liquid actually contained within the pump chamber times the temperature deviation from the initial condition is expressed as a voltage on line 276. This voltage is connected to potentiometer control 278 upon which the operator sets the difference between the thermal expansion coefficient of the contained liquid and the (always constant) expansion coefficient of the rest of the pump. The output of this potentiometer, on line 280, is a voltage representing the piston position change necessary to compensate for the temperature change. This is led by resistor 282 to the position error amplifier input terminal 284, the inverting input of operational amplifier 266. The output of the amplifier 266 represents the position error of the piston including both the thermal volume error and the volume error due to accumulated slight errors in the velocity-feedback control of the piston.

If the cylinder is held at the constant temperature by means such as shown in FIGS. 4 and 5, the temperature-error sensing thermistor should be moved to a location other than that of the heat conductor 132. Even with temperature control of the cylinder and cylinder cap surrounding the liquid-holding volume of the pump, changes in ambient temperature will still have a small residual effect which will displace liquid in or out of the outlet tube 19. For example, such error could come from inability to perfectly balance the temperature coefficients of the frame member to the temperature coefficients of lead screw and piston push tube. In such case, the thermistor should be relocated to a different part of the pump, determined experimentally according to the exact pump design.

Of course, a microprocessor may be used to accomplish some or all of the above functions by connecting it to interface with the sensed signals and to receive other programmed information.

From the above description it may be understood that the chromatographic system of this invention has several advantages, such as: (1) it prevents errors in flow rate due to changes in ambient temperature; (2) it compensates for changes in flow rate due to temperature changes; and (3) it permits more reliable and effective operation of microscale chromatographs.

Although a preferred embodiment of the invention has been described with some particularity, many modifications and variations in the embodiment are possible without deviating from the above teachings. Therefore, it is to be understood that, within the scope of the appended claims, the invention may be practiced otherwise than specifically described.

What is claimed is:

1. A method of compensating for changes in temperature during the operation of a microscale chromatograph comprising the steps of:
forcing fluid from a pumping system having a chamber into a chromatographic means by changing the size of the chamber;
measuring changes in temperature;
adjusting the rate of change of the size of the chamber to maintain a predetermined rate of flow by correcting for errors caused by changes in temperature;
the step of changing the size of the chamber including the step of driving the piston of a pump at a controlled rate; and
the step of adjusting the rate of change including the steps of calculating the change necessary in the rate of change of the size of the chamber, and altering the rate of change of the piston to provide for such change.

2. A method according to claim 1 in which the step of adjusting the rate of change includes the steps of:
calculating changes in the rate of flow of fluid caused by said changes in ambient temperature; and
controlling the speed of said pump to compensate for such changes in flow rate.

3. A method according to claim 2 in which the step of calculating change includes the steps of:
measuring the temperature at a starting time;
obtaining the difference between the starting time temperature and changes in temperature during pumping;
measuring the volume of fluid in the pump during pumping;
multiplying the temperature change by the volume of fluid to obtain a factor proportional to the change of volume of the fluid; and
multiplying the change of volume of fluid by a factor adjusted to provide an indication of the volume error due to the differing coefficient of temperature expansion of the fluid and the walls of the pumping system.

4. A method according to claim 2 in which the step of calculating change includes the steps of:
measuring the temperature at a starting time;
obtaining the difference between the starting time temperature and changes in temperature during pumping by subtraction in a microprocessor;
mesuring the volume of fluid in the pump during pumping;
multiplying the temperature change by the volume of fluid to obtain a factor proportional to the change of volume of the fluid in a microprocessor; and
multiplying the change of volume of fluid by a factor adjusted to provide an indication of the volume error due to the differing coefficient of temperature expansion of the fluid and the walls of the pumping system in a microprocessor.

5. A method of compensating for changes in temperature during the operation of a microscale chromatograph comprising the steps of:
forcing fluid from a pumping system having a chamber into a chromatographic means by changing the size of the chamber;
measuring changes in temperature;
adjusting the rate of change of the size of the chamber to maintain a predetermined rate of flow by correcting for errors caused by changes in temperature; and
the step of adjusting the rate of change including the steps of calculating changes in the rate of flow of fluid caused by said changes in ambient temperature and controlling the speed of said pumping system to compensate for such changes in flow rate.

6. A method according to claim 5 in which the step of calculating change includes the steps of:
measuring the temperature at a starting time;
obtaining the difference between the starting time temperature and changes in temperature during pumping;
measuring the volume of fluid in the pumping system during pumping;
multiplying the temperature change by the volume of fluid to obtain a factor proportional to the change of volume of the fluid; and
multiplying the change of volume of fluid by a factor adjusted to provide an indication of the volume error due to the differing coefficient of temperature expansion of the fluid and the walls of the pumping system.

7. Apparatus comprising:
pumping system means;
chromatographic means for receiving fluid from said pumping system means;
said pumping system means including a positive displacement pump;
means for measuring changes in temperature in said positive displacement pump;
means for adjusting the rate of pumping of said pumping system means to correct for errors caused by changes in temperature; and
the means for adjusting the rate of pumping including means for calculating changes in the rate of flow of fluid caused by changes in temperature and means for controlling the speed of said pumping system means to compensate for said changes in flow rates.

8. Apparatus according to claim 7 in which said means for calculating comprises:
means for measuring the volume of the fluid in said pumping system means;
means for measuring the changes in temperature; and
means for calculating from said changes in temperature and volume the error in flow rate caused by said changes in volume of fluid.

9. Apparatus according to claim 8 in which said means for measuring the volume includes:
tachometer means;
motor means for driving said pumping system;
means for connecting said tachometer means to said motor means to provide a signal representing the speed of said motor means; and
means for determining the volume in said pumping system means from said speed of said motor means and from the starting time of a cycle.

10. Apparatus according to claim 9 in which said means for measuring the volume includes:
switch means for determining a predetermined position of a piston in said pumping system means;
means for using said predetermined position to establish a reference volume; and
means for correlating said reference volume with said motion of said motor to provide a signal indicating the volume of said pumping system means.

11. A method of compensating for temperature changes of the solvent in a microscale liquid chromatograph driven by a syringe pump comprising the steps of:
pumping fluid from the syringe pump into the microscale chromatographic system;
measuring a temperature related to the temperature of the fluid in the cylinder of the syringe pump;
detecting changes in said measured temperature; and
changing the transfer of heat between said syringe pump and another location in response to changes in said measured temperature whereby the temperature of the fluid and the syringe pump are stabilized.

12. A method according to claim 11 in which the step of measuring a temperature related to the temperature of the fluid in the cylinder includes the step of sensing the temperature of the cylinder wall of the syringe pump.

13. A method according to claim 12 in which the step of changing the transfer of heat includes the step of applying electrical current through a resistance winding in intimate contact with the cylinder of the pump.

14. A method according to claim 13 in which the step of changing the transfer of heat includes the step of stabilizing the temperature of the pump at a temperature above ambient temperature.

15. A method according to claim 11 in which the step of changing the transfer of heat includes the step of applying electrical current through a resistance winding in intimate contact with the cylinder of the pump.

16. A method according to claim 15 in which the step of changing the transfer of heat includes the step of stabilizing the temperature of the pump at a temperature above ambient temperature.

17. A method according to claim 11 in which the step of changing the transfer of heat includes the step of stabilizing the temperature of the pump at a temperature above ambient temperature.

18. A microscale chromatograph comprising:
pumping system means;
chromatographic means for receiving fluid from the pumping system means;
said pumping system means including a syringe-type pump having a cylinder with the capacity for holding liquid at least ten times the capacity for holding liquid of the chromatographic means, whereby differences in the temperature coefficient of the expansion of the fluid and the cylinder cause discrepancies in the accuracy of flow rate control of the pumping system in supplying fluid to the chromatographic means;
means for measuring the temperature of said cylinder;
means for applying heat to said cylinder; and
control means electrically connected to said means for measuring the temperature of said cylinder and the means for supplying heat to said cylinder for maintaining the temperature of said cylinder slightly above ambient temperature.

19. Apparatus according to claim 18 in which said means for measuring temperature includes a temperature measuring device mounted in contact with the cylinder walls of said pump.

20. Apparatus according to claim 19 in which said means for heating includes heating coil means within said pump.

21. Apparatus according to claim 18 in which said means for heating includes heating coil means within said pump.

22. A method for compensating for flow rate errors caused by temperature changes in a liquid chromatograph comprising the steps of:
maintaining the temperature within a pumping means of said chromatograph at a level slightly above ambient temperature; and
measuring temperature changes across the chromatographic run and changing the speed of pumping to compensate for the difference in coefficients of expansion of said volume of liquid within said pumping means and the temperature coefficient of expansion of said pumping mean's solid parts.

23. A method according to claim 22 further comprising the steps of:
forcing fluid from a pumping means having a chamber into a chromatographic means by changing the size of the chamber;
measuring changes in temperature; and
adjusting the rate of change of the size of the chamber to maintain a predetermined rate of flow by correcting for errors caused by changes in temperature.

24. A method according to claim 23 in which:
the step of changing the size of the chamber includes the step of driving the piston of a pumping means at a controlled rate; and
the step of adjusting the rate of change includes the steps of calculating the change necessary in the rate of change of the size of the chamber, and altering the rate of change of the piston to provide for such change.

25. A method according to claim 24 in which the step of adjusting the rate of change includes the steps of:
calculating changes in the rate of flow of fluid caused by changes in ambient temperature; and
controlling the speed of said pumping means to compensate for such changes in flow rate.

26. A method according to claim 25 in which the step of calculating change includes the steps of:
measuring the temperature at a starting time;
obtaining the difference between the starting time temperature and changes in temperature during pumping;
measuring the volume of fluid in the pump during pumping;
multiplying the temperature change by the volume of fluid to obtain a factor proportional to the change of volume of the fluid; and
multiplying the change of volume of fluid by a factor adjusted to provide an indication of the volume error due to the differing coefficient of temperature expansion of the fluid and the solid parts of the pumping system.

27. A method according to claim 26 in which the steps of maintaining the temperature of the chromatograph at a level comprises the steps of:
measuring a temperature related to the temperature of the fluid in the cylinder of the pumping means;
detecting changes in said measured temperature; and
changing the transfer of heat between said pumping means and another location in response to changes in said measured temperature whereby the temperature of the fluid and the pumping means are stabilized.

28. A method according to claim 27 in which the step of measuring a temperature related to the temperature of the fluid in the cylinder includes the step of sensing the temperature of the cylinder wall of the pumping system.

29. A method according to claim 28 in which the step of changing the transfer of heat includes the step of applying electrical current through a resistance winding in intimate contact with the pumping system.

30. Apparatus comprising:
a pumping system;
a chromatographic means for receiving fluid from said pumping system;
said pumping system including at least one positive displacement pump having a cylinder with a capacity for holding fluid which is at least ten times the capacity for containing fluid of said chromatographic means whereby the differences in the temperature coefficient of expansion of the fluid within said positive displacement pump and the walls of said pump tend to cause errors in flow rate when there are temperature changes;
means for maintaining the temperature of said positive displacement pump slightly above ambient temperature; and
means for changing the rate of pumping of said pumping system to compensate for the differences in the temperature coefficient of expansion of said fluid and the structural parts of said positive displacement pump.

31. Apparatus according to claim 30 in which said means for changing the rate of pumping includes:
means for measuring changes in temperature in said positive displacement pump; and
means for adjusting the rate of pumping of said pumping system means to correct for errors caused by changes in temperature.

32. Apparatus according to claim 31 in which the means for changing the rate of pumping includes means for calculating changes in the rate of flow of fluid caused by changes in temperature and means for controlling the speed of said pump system to compensate for said changes in flow rates.

33. Apparatus according to claim 32 in which said means for calculating comprises:
means for measuring the volume of the fluid in said pumping system;
means for measuring the changes in temperature; and
means for calculating from said changes in temperature and volume the error in flow rate caused by said changes in volume of fluid.

34. Apparatus according to claim 33 in which said means for measuring the volume includes:
tachometer means;
motor means for driving said pumping system;
means for connecting said tachometer means to said motor means to provide a signal representing the speed of said motor means; and
means for determining the volume in said pump from said speed of said motor means and from the starting time of a cycle.

35. Apparatus according to claim 34 in which said means for measuring the volume includes:
switch means for determining a predetermined position of a piston in said pump;
means for using said predetermined position to establish a reference volume; and
means for correlating said reference volume with said motion of said motor to provide a signal indicating the volume of said pump.

36. Apparatus according to claim 35 in which said means for maintaining the temperature includes:
means for measuring the temperature of said cylinder;
means for applying heat to said cylinder; and
control means electrically connected to said means for measuring the temperature of said cylinder and the means for supplying heat to said cylinder for maintaining the temperature of said cylinder slightly above ambient temperature.

37. Apparatus according to claim 36 in which said means for heating includes heating coil means within said pump.

* * * * *